(12) United States Patent
Lynch

(10) Patent No.: US 12,343,166 B2
(45) Date of Patent: Jul. 1, 2025

(54) SIGNAL MEASURING APPARATUS AND SYSTEM

(71) Applicant: Prevayl Innovations Limited, Manchester (GB)

(72) Inventor: Michael John Lynch, Cheshire (GB)

(73) Assignee: Prevayl Innovations Limited, Wilmslow (GB)

( * ) Notice: Subject to any disclaimer, the term of this patent is extended or adjusted under 35 U.S.C. 154(b) by 468 days.

(21) Appl. No.: 17/796,949

(22) PCT Filed: Feb. 24, 2021

(86) PCT No.: PCT/GB2021/050449
§ 371 (c)(1),
(2) Date: Aug. 2, 2022

(87) PCT Pub. No.: WO2021/170994
PCT Pub. Date: Sep. 2, 2021

(65) Prior Publication Data
US 2023/0309926 A1  Oct. 5, 2023

(30) Foreign Application Priority Data

Feb. 26, 2020  (GB) .................................. 2002716.5
Feb. 26, 2020  (GB) .................................. 2002717.3

(51) Int. Cl.
*A61B 5/00* (2006.01)

(52) U.S. Cl.
CPC ............ *A61B 5/6804* (2013.01); *A61B 5/002* (2013.01); *A61B 2562/12* (2013.01)

(58) Field of Classification Search
CPC .... A61B 5/6804; A61B 5/002; A61B 2562/12
See application file for complete search history.

(56) References Cited

U.S. PATENT DOCUMENTS

| 6,646,336 B1 | 11/2003 | Marmaropoulos |
| 6,943,061 B1 | 9/2005 | Sirinorakul |

(Continued)

FOREIGN PATENT DOCUMENTS

| CN | 110123305 | 8/2019 |
| GB | 2555592 | 2/2019 |

(Continued)

OTHER PUBLICATIONS

Search Report received in GB2002717.3 mailed Aug. 17, 2020.
(Continued)

*Primary Examiner* — Thanh Tam T Le
(74) *Attorney, Agent, or Firm* — Suzannah K. Sundby, Esq.; Canady + Lortz LLP

(57) ABSTRACT

A wearable article (1) including a sensor assembly (104) for sensing signals, such as biosignals, that are associated with a wearer of the wearable article. The sensor assembly comprises at least one sensor (106, 108) for sensing the associated signals, and a sensor interface (110) coupled to the at least one sensor and configured to wirelessly couple sensor data received from the at least one sensor to an electronic device. The electronic device can be a mobile device such as a cellular radio telephone. The sensor interface includes sensing electronics which incorporates a sensor interface antenna configured for wireless coupling to an electronic device antenna when the electronic device and the sensor interface are in close proximity. The sensing electronics is configured to collate sensor data from the at least one sensor and to wirelessly communicate the sensor data to the electronic device by the wireless, coupling.

23 Claims, 7 Drawing Sheets

(56) References Cited

U.S. PATENT DOCUMENTS

| | | | |
|---|---|---|---|
| 8,022,522 B1 | 9/2011 | Liou | |
| 8,608,984 B1 * | 12/2013 | Taranekar | A61B 5/28 |
| | | | 252/514 |
| 9,138,191 B1 | 9/2015 | Kaskoun | |
| 10,310,558 B2 * | 6/2019 | Lewallen | G06F 1/1656 |
| 10,321,832 B2 * | 6/2019 | Berg | A61B 5/1118 |
| 10,398,376 B2 * | 9/2019 | Berg | A61B 5/6804 |
| 10,758,184 B2 * | 9/2020 | Gupta | A61B 5/296 |
| 10,993,660 B2 * | 5/2021 | Palley | A61B 5/6804 |
| 11,219,396 B2 * | 1/2022 | Berg | A61B 5/6804 |
| 11,298,078 B2 * | 4/2022 | Oehler | A61B 5/6804 |
| 2003/0211797 A1 | 11/2003 | Hill | |
| 2007/0164409 A1 | 7/2007 | Holland | |
| 2014/0135593 A1 | 5/2014 | Jayalth | |
| 2015/0015249 A1 | 1/2015 | Ausserlechner | |
| 2017/0053856 A1 | 2/2017 | Luan | |
| 2018/0090449 A1 | 3/2018 | Jeong | |
| 2018/0107244 A1 | 4/2018 | Fujie | |
| 2018/0138616 A1 | 5/2018 | Dumont | |
| 2018/0295720 A1 | 10/2018 | Aleksov | |
| 2022/0384315 A1 | 12/2022 | Lynch | |

FOREIGN PATENT DOCUMENTS

| | | |
|---|---|---|
| GB | 2589567 | 6/2021 |
| GB | 2592391 | 9/2021 |
| GB | 2593479 | 9/2021 |
| GB | 2593674 | 10/2021 |
| WO | 2016051268 | 4/2016 |
| WO | 2016054057 | 4/2016 |
| WO | 2019020550 | 1/2019 |
| WO | 2019134031 | 7/2019 |
| WO | 2019197892 | 10/2019 |
| WO | 2021105676 | 6/2021 |

OTHER PUBLICATIONS

International Search Report received in PCT/GB2021/050449 mailed May 11, 2021.
Written Opinion received in PCT/GB2021/050449 mailed May 11, 2021.
Search Report received in GB1917331.9 mailed Apr. 6, 2020.
Examination Report received in GB2002716.5 mailed Mar. 9, 2021.
Examination Report received in GB2002716.5 mailed Mar. 23, 2021.
Examination Report received in GB2002716.5 mailed Mar. 18, 2022.
Examination Report received in GB2002716.5 mailed May 16, 2022.
Search and Examination Report received in GB2002716.5 mailed Aug. 18, 2020.
Search Report received in GB2004244.6 mailed Sep. 16, 2020.
Search Report received in GB2004245.3 mailed Sep. 16, 2020.
Prosecution of U.S. Appl. No. 17/772,242.

* cited by examiner

SIGNAL MEASURING APPARATUS AND SYSTEM

The present invention is directed towards a biosignals measuring apparatus incorporating a sensor assembly and an electronic device, a sensor assembly, a sensor interface, and a wearable article incorporating a sensor interface, particularly, although not exclusively, for sensing biosignals from a wearer of the wearable article.

BACKGROUND

Wearable articles, such as garments, incorporating sensors are wearable electronics used to measure and collect information from a wearer. Such wearable articles are commonly referred to as 'smart clothing'. It is advantageous to measure biosignals of the wearer during exercise, or other scenarios.

It is known to provide a garment, or other wearable article, to which a device (i.e. an electronic module, and/or related components) is attached in a prominent position, such as on the chest or between the shoulder blades. Advantageously, the device is a detachable device. The device is configured to process the incoming signals, and the output from the processing is stored and/or displayed to a user in a suitable way A sensor senses a biosignal such as electrocardiogram (ECG) and the biosignals are coupled to the device, via an interface.

The sensors may be coupled to the interface by means of conductors which are connected to terminals provided on the interface to enable coupling of the signals from the sensor to the interface.

The device includes drive and sensing electronics comprising components and associated circuitry, to provide the required functionality.

The number of conductors between the sensors and the device will depend upon the number of sensors.

The number of conductors dictates the size and fixing of the device to the garment. The more connection points that exist, the likelihood of the connection between the sensors failing increases, especially as one half of the connection i.e., the interface (which is integrated into the garment) is intended to be washed.

More connections will result in more complexity in design, manufacture and test.

Having a fixed number of connection points locks the design for the full product lifecycle and potentially means that future enhancements to either the garment or electronics may not be compatible with the existing design.

SUMMARY

According to a first aspect of the present invention, there is provided a wearable article including a sensor assembly for sensing biosignals associated with a wearer of the wearable article. The sensor assembly comprises at least one sensor for sensing the biosignals, and a sensor interface coupled to the at least one sensor and configured to wirelessly couple biosignal data from the at least one sensor to an electronic device. The sensor interface comprises sensing electronics including a sensor interface antenna configured for wireless coupling to an antenna of an electronic device when the electronic device and the sensor interface are in close proximity. The sensing electronics is configured to collate the biosignal data and to wirelessly communicate the biosignal data to the electronic device by means of the wireless coupling. The sensor interface comprises a printed circuit board onto which the sensing electronics is mounted. The printed circuit board has a region of increased flexibility. The printed circuit board includes at least one terminal to which the at least one sensor and the sensing electronics are coupled.

Alternatively, the printed circuit board may be rigid or a rigid flexible printed circuit board. The at least one terminal may be provided on the region of increased flexibility. The printed circuit board may be thinner at the region of increased flexibility. Alternatively, a reinforcing layer may be provided at a region of reduced flexibility.

The reinforcing layer may have a thickness of 0.05 mm or more. The thickness may be between 0.05 mm and 10 mm and more preferably between 0.05 mm and 3 mm. Alternatively, the thickness may be 0.1 mm and 1 mm.

The reinforcing layer may be made from a polyamide material.

The printed circuit board may have a thickness in the region of reduced flexibility which is 0.05 mm or greater than the thickness of the printed circuit board in region of increased flexibility.

The printed circuit board may be integrated within a portion of the wearable article.

Preferably, the at least one sensor is coupled to the sensor interface by means of a respective conductor and the respective conductor is connected to the at least one printed circuit board terminal.

Preferably, the printed circuit board comprises a plurality of terminals and the sensor assembly comprises a plurality of sensors, each of the sensors being coupled to the sensor interface by means of a respective conductor and the respective conductor is connected one of the plurality of printed circuit board terminals.

The plurality of terminals may be provided on the region of increased flexibility.

Preferably, the printed circuit board is fixed to the surface of the wearable article by means of thread or yarn. Alternatively, the sensor interface includes rivets arranged to rivet the printed circuit board to the surface of the garment.

Preferably, the sensor interface includes a housing arranged to encase the sensing electronics.

Preferably, the housing is made of a flexible material. Preferably, the flexible material is silicone rubber.

Preferably, the flexible material has a shore hardness of 90 or below. More preferably, the shore hardness is 85 or below, even more preferably 80 or below, or below 70.

Preferably, the respective conductor is formed from a conductive yarn.

Preferably, the conductive yarn is stitched through a respective terminal on the printed circuit board. The conductive yarn may be stitched through the respective terminal on the printed circuit board at the region of increased flexibility.

Alternatively, the respective conductor is a conductive transfer.

Preferably, the terminating portions of the conductive transfers are configured in a pattern that corresponds with the terminals on the printed circuit board.

Preferably, the respective conductor is retained against a respective terminal by a pressure fit.

Preferably, the sensor interface antenna is inductively coupled to the electronic device antenna.

Preferably, the sensing electronics is configured to receive power from the electronic device by means of the inductive coupling.

Preferably, the sensing electronics includes a controller, and an interface arranged to couple the sensor data from the at least one sensor to the sensing electronics and a wireless interface configured to couple the sensor data to the sensor interface antenna for wireless communication to the electronic device antenna.

Preferably, the wireless interface includes a memory configured to store data. Preferably the data stored in the memory is identification data associated with the wearable article, configuration and control bits, or user data, The memory may be an erasable programmable read-only memory (EPROM), an electrically erasable programmable read-only memory (EEPROM) or a floating-gate memory such as flash memory. This has advantages that include the ability to work reliably in a relatively high impedance signal line and requiring a relatively low power input compared to other memory types.

Preferably, the wireless interface is a short-range communication module. The short-range communication module may comprise one or more of a near field communication module, a Bluetooth® module, Bluetooth® Low Energy, Bluetooth® Mesh, Bluetooth® 5, Thread, Zigbee®, IEEE 802.15.4, and Ant communication module.

Preferably, the at least one conductor is terminated in a delineated region of the wearable article and wherein the delineation is shown by a visible demarcation.

Preferably, the wearable article includes an electronic device holder arranged to at least temporarily retain the electronic device such that the electronic device and the sensor interface are arranged in close proximity.

Preferably the electronic device holder comprises a pocket into which the electronic device can be placed such that the electronic device and the sensor interface are arranged in close proximity.

Preferably, the associated signals are biosignals. Preferably, the sensors are motion sensors or position locations sensors such GPS sensors.

Preferably, the wireless coupling of the sensor interface antenna to the electronic device antenna is inductive coupling.

According to a second aspect of the present invention, there is provide a method of manufacturing a wearable article including a sensor assembly for sensing biosignals associated with a wearer of the wearable article, the method including the steps of:

forming at least one sensor on the wearable article;
forming a printed circuit board having a region of increased flexibility;
mounting sensor electronics on the printed circuit board, the sensing electronics including a first antenna configured for wireless coupling to an antenna of an electronic device and at least one terminal to which the at least one sensor and the sensing electronics are coupled;
forming at least one conductor on the wearable article so as to electrically couple the at least one sensor and the at least one terminal; and
forming a housing around the printed circuit board to encase the sensor electronics for sensing the associated signals to the sensor interface.

Preferably, the at least one terminal is formed on the region of increased flexibility Preferably, the printed circuit board is formed to be thinner at the region of increased flexibility.

Preferably, the printed circuit board includes a region of reduced flexibility. The region of reduced flexibility may be formed by adding a reinforcing layer.

Preferably, the sensing electronics is mounted on the printed circuit board at the region of reduced flexibility.

Preferably, the method includes the step of attaching the printed circuit board to the surface of the wearable article.

Preferably, the method includes the step of sewing the printed circuit board onto the wearable article. Alternatively, the method includes the step of embroidering the printed circuit board onto the wearable article. In another alternative, the printed circuit board is riveted onto the wearable article.

Preferably, the printed circuit board includes an adhesive surface, and the method includes the step of adhering the printed circuit board to the surface of the wearable article at the adhesive surface. Preferably, the method includes the step of covering the printed circuit board with an epoxy resin prior to forming the housing around the printed circuit board.

Preferably, the at least one conductor is formed on the wearable article prior attaching the printed circuit board to the surface of the garment.

Preferably, the at least one conductor is terminated in a region of the wearable article.

Preferably, this region is delineated. Preferably, the delineation is shown by a visible demarcation. The visible demarcation may be formed by means of yarn or thread of a different colour or texture to that of the wearable article.

Preferably, the housing is formed from a flexible material. Preferably, the flexible material is silicone rubber.

Preferably, the housing is formed by injection moulding.

Preferably, the at least one conductor is made of conductive yarn.

Preferably, the conductive yarn is stitched through a respective terminal on the printed circuit board.

Alternatively, the at least one conductor is formed as a conductive transfer.

Preferably, the method includes the step of forming an electronic device holder in the wearable article into which the electronic device can be placed such that the electronic device and the sensor interface are in close proximity.

Preferably, the electronic device holder is formed as a pocket.

According to a third aspect of the present invention, there is provided a system for measuring biosignals associated with a wearer of a wearable article, the system comprising the wearable article and an electronic device, the wearable article including a sensor assembly comprising at least one sensor for sensing the biosignals, and a sensor interface coupled to the at least one sensor and comprising sensing electronics including a sensor interface antenna, and the electronic device comprising drive electronics including an electronic device antenna, the sensor interface antenna and the electronic device antenna being configured for wireless coupling when the electronic device and the sensor interface are in close proximity, the sensing electronics being configured to collate biosignal data from the at least one sensor and to wirelessly communicate the biosignal data to the electronic device via the sensor interface antenna and the electronic device antenna by means of the wireless coupling, the sensor interface comprising a printed circuit board onto which the sensing electronics is mounted, the printed circuit board having a region of increased flexibility, the printed circuit board including at least one terminal to which the at least one sensing electrode and the sensing electronics are coupled.

The at least one terminal may be provided on the region of increased flexibility.

The printed circuit board may be thinner at the region of increased flexibility. Alternatively, a reinforcing layer may be provided at a region of reduced flexibility. The sensing electronics may be provided on the region of reduced flexibility.

The printed circuit board may be integrated within a portion of the wearable article.

Alternatively, the printed circuit board may be rigid or a rigid flexible printed circuit board.

Preferably, the at least one sensor is coupled to the sensor interface by means of a respective conductor and the respective conductor is connected to the at least one printed circuit board terminals.

Preferably, the printed circuit board comprises a plurality of terminals and the sensor assembly comprises a plurality of sensors, each of the sensors being coupled to the sensor interface by means of a respective conductor and wherein the respective conductor is connected one of the plurality of printed circuit board terminals.

The plurality of terminals may be provided on the region of increased flexibility.

Preferably, the sensor interface includes a housing arranged to encase the sensing electronics.

Preferably, the housing is made of a flexible material. Preferably, the flexible material is silicone rubber.

Preferably, the flexible material has a shore hardness of 90 or below. More preferably, the shore hardness is 85 or below, even more preferably 80 or below, or below 70.

Preferably, the at least one conductor is formed from a conductive yarn.

Preferably, the conductive yarn is stitched through a respective terminal on the printed circuit board. The conductive yarn may be stitched through the respective terminal on the printed circuit board at the region of increased flexibility.

Alternatively, the respective conductor is a conductive transfer.

Preferably, the terminating portions of the conductive transfers are configured in a pattern that corresponds with the terminals on the printed circuit board.

Preferably, the respective conductor is retained against a respective terminal by a pressure fit.

Preferably, the sensing electronics is configured to receive power from the electronic device by means of the inductive coupling.

Preferably, the sensing electronics includes a controller, and an interface arranged to couple the sensor data from the at least one sensor to the sensing electronics and a wireless interface configured to couple the sensor data to the sensor interface antenna for wireless communication to the electronic device antenna.

Preferably, the wireless interface is a short-range communication module. The short-range communication module may comprise one or more of a near field communication module, a Bluetooth® module, Bluetooth® Low Energy, Bluetooth® Mesh, Bluetooth® 5, Thread, Zigbee®, IEEE 802.15.4, and Ant communication module. Other wireless communication protocols can also be used, such as used for communication over: a wireless wide area network (WWAN), a wireless metro area network (WMAN), a wireless local area network (WLAN), a wireless personal area network (WPAN), a Global Navigation Satellite System (GNSS), a cellular communication network, or any other electromagnetic RF communication protocol.

Preferably, the wearable article includes an electronic device holder arranged to at least temporarily retain the electronic device such that the electronic device and the sensor interface are arranged in close proximity.

Preferably the electronic device holder comprises a pocket into which the electronic device can be placed such that the electronic device and the sensor interface are arranged in close proximity.

Preferably, the electronic device is a mobile device and more preferably, a cellular radio telephone.

According to another aspect of the present invention, there is provided a wearable article including a sensor assembly for sensing signals associated with a wearer of the wearable article, the sensor assembly comprising at least one sensor for sensing the associated signals, and a sensor interface coupled to the at least one sensor and configured to wirelessly couple sensor data received from the at least one sensor to an electronic device, the sensor interface comprising sensing electronics, including a sensor interface antenna configured for wireless coupling to a mobile device antenna when the electronic device and the sensor interface are in close proximity, wherein the sensing electronics is configured to collate sensor data from the at least one sensor and to wirelessly communicate the sensor data to the mobile device by means of the wireless coupling.

The object of the present invention is to provide an improved measuring apparatus, sensor assembly and device interface and wearable article incorporating a device interface.

The present invention has the advantage that the sensing electronics is provided in the garment rather than being co-located with the drive electronics. The drive electronics communicates with this sensing circuitry by the means of a wireless near field interface.

The sensor interface has no dedicated power source and derives its power from the mobile device through inductive coupling between the mobile device antenna and the sensor interface antenna. This removes the need for additional power source on the garment. The microcontroller simply operates as a data gatherer without carrying out any complex processing, thus minimising power usage by the sensing electronics.

This enables the drive electronics, and therefore the mobile device, to be utilised with different sensor configurations, sensor types and so on. For example, the same mobile device can be used with a garment having a two sensor ECG configuration, a multi-sensor ECG configuration, and an EMG configuration, for example. Another example may be a garment that has a number of inertial measurement units built into it for motion conductor's purposes.

The use of a wireless interface such as this allows for the drive electronics to act primarily as a data gatherer/gateway to a remote platform for more detailed processing and analysis.

Having the same drive electronics operate with several different garment configurations allows the drive electronics to be manufactured in a higher volume, thus meeting price breaks and remaining lower in cost. The drive electronics may comprise a cellular radio telephone.

The use of a printed circuit board with a number of terminals, all or some of which can be used, enables a variety of types and numbers of sensors to be attached to the sensor interface. This allows for volume manufacture of a single type of garment which can be used for different sensing requirements.

BRIEF DESCRIPTION OF THE DRAWINGS

Examples of the present disclosure will now be described with reference to the accompanying drawings, in which.

DETAILED DESCRIPTION

Figure 1:
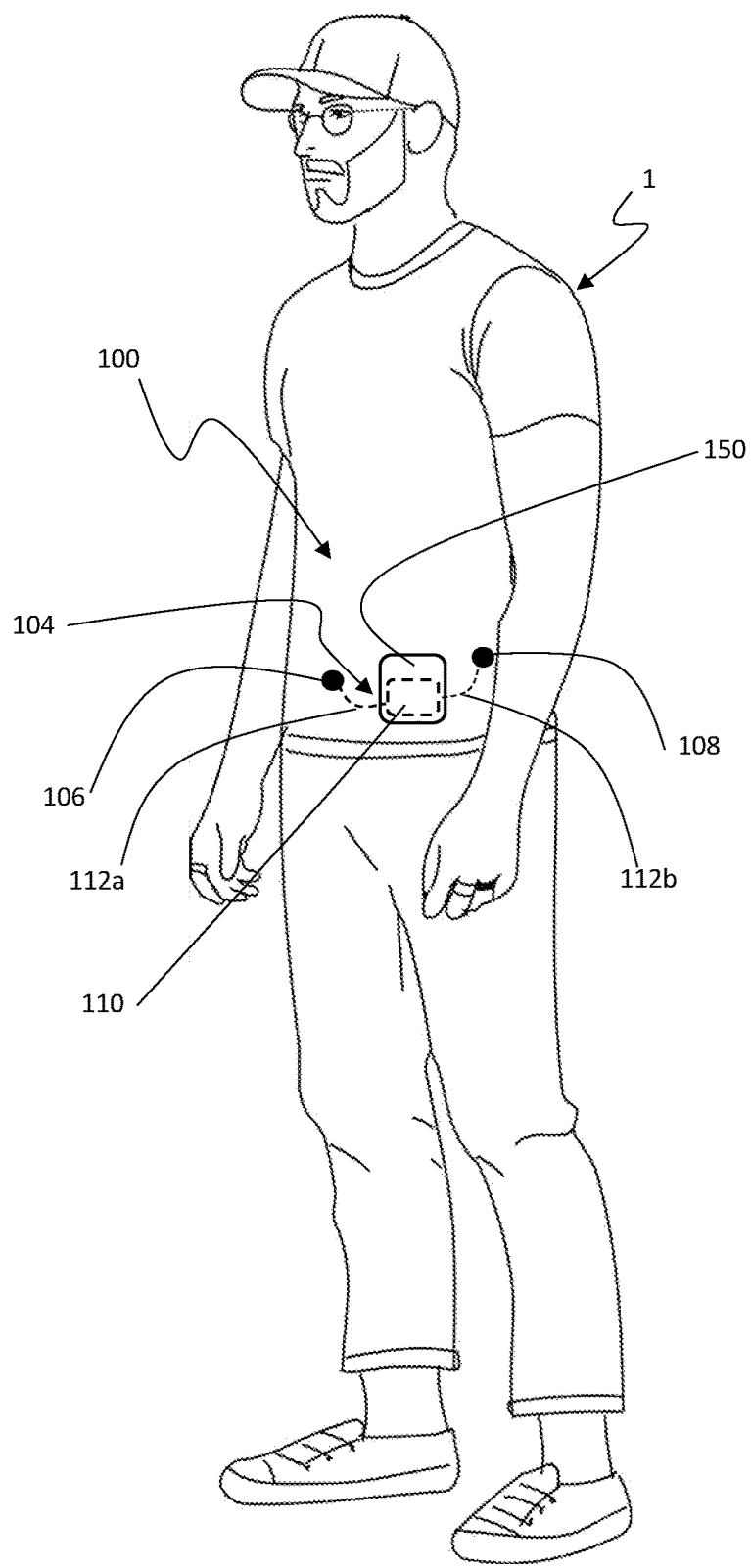
FIG. 1 illustrates a sensor interface integrated into a wearable garment.
Figure 2:
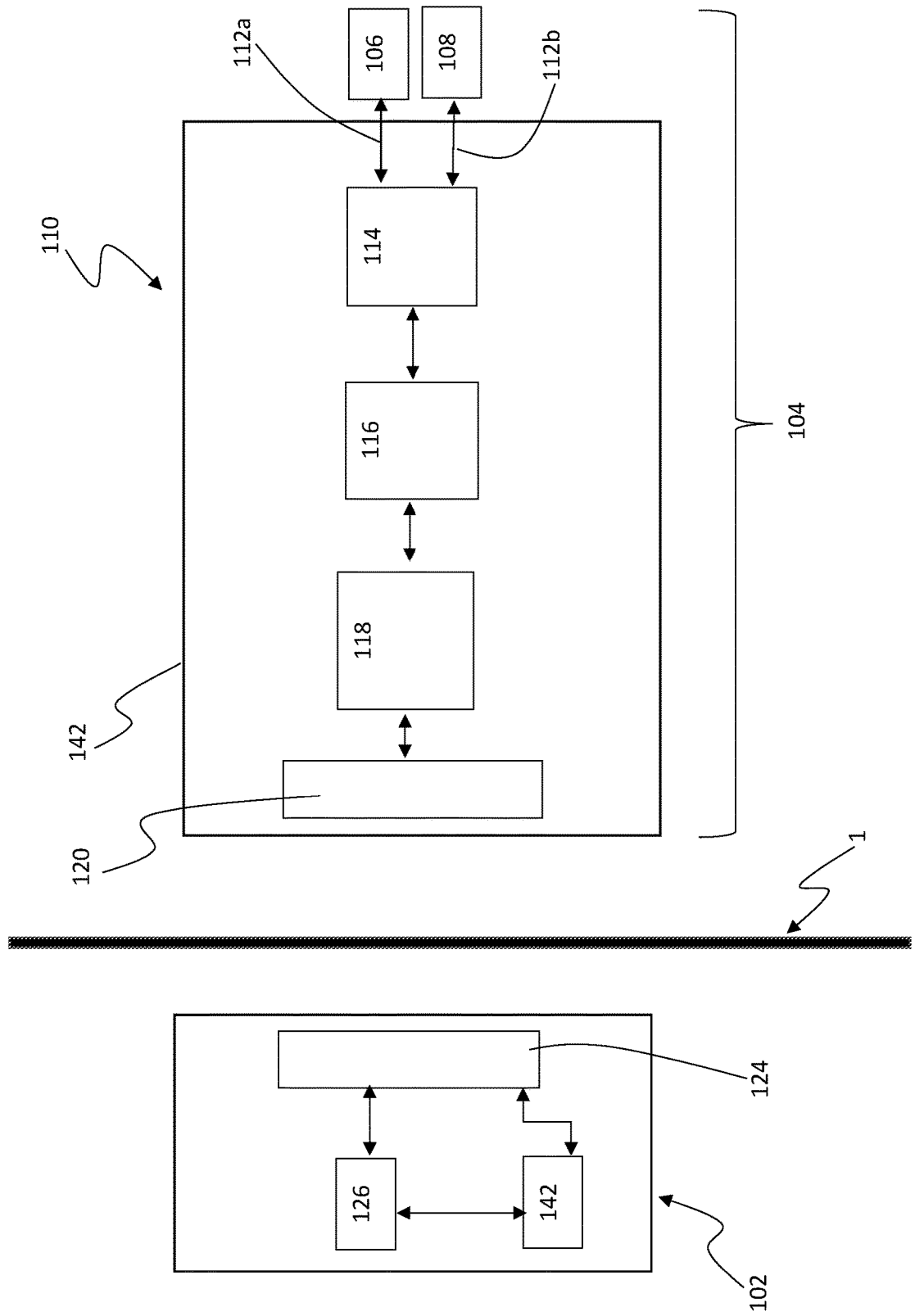
FIG. 2 is a schematic block diagram illustrating the functional components of a measuring apparatus comprising a sensor assembly and a mobile device.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of device interface which may be worn by a user such as a smart watch, necklace, garment, bracelet, or glasses. The wearable article may be a textile article. The wearable article may be a garment. The garment may refer to an item of clothing or apparel. The garment may be a top.

The top may be a shirt, t-shirt, blouse, sweater, jacket/coat, or vest. The garment may be a dress, garment brassiere, shorts, pants, arm or leg sleeve, vest, jacket/coat, glove, armband, underwear, headband, hat/cap, collar, wristband, stocking, sock, or shoe, athletic clothing, personal protective equipment, swimwear, wetsuit or dry suit.

The term "wearer" includes a user who is using, wearing, or otherwise holding, the wearable article.

The type of wearable garment may dictate the type of biosignals to be detected. For example, a hat or cap may be used to detect electroencephalogram or magnetoencephalogram signals.

The wearable article/garment may be constructed from a woven or a non-woven material. The wearable article/garment may be constructed from natural fibres, synthetic fibres, or a natural fibre blended with one or more other materials which can be natural or synthetic. The yarn may be cotton. The cotton may be blended with polyester and/or viscose and/or polyamide according to the application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment.

The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

The garment has sensing units provided on an inside surface which are held in close proximity to a skin surface of a wearer wearing the garment. This enables the sensing units to measure biosignals for the wearer wearing the garment.

The sensing units may be arranged to measure one or more biosignals of a wearer wearing the garment.

"Biosignal" as referred to throughout the present disclosure may refer to signals from living beings that can be continually measured or monitored. Biosignals may be electrical or non-electrical signals. Signal variations can be time variant or spatially variant.

Sensing components may be used for measuring one or a combination of bioelectrical, bioimpedance, biochemical, biomechanical, bioacoustics, biooptical or biothermal signals of the wearer 600. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG). The biochemical measurements include glucose/lactose measurements which may be performed using chemical analysis of the wearer 600's sweat. The biomechanical measurements include blood pressure. The bioacoustics measurements include phonocardiograms (PCG). The biooptical measurements include orthopantomogram (OPG). The biothermal measurements include skin temperature and core body temperature measurements.

In the embodiment described herein, a garment 1 is for use in measuring biosignals of a wearer.

In the present embodiment of the invention, a garment 1 includes a sensor assembly 104 configured for wireless communication with a mobile device 102. The mobile device 102 and sensor assembly 104 are configured for wireless communication when the sensor assembly 104 and the mobile device 102 are in near field proximity.

The sensor assembly 104 comprises a sensor interface 110, and first and second sensing electrodes 106, 108 which are connected to the sensor interface 110 by means of respective conductors 112a, 112b. The first and second sensing conductors 112a, 112b are therefore configured to connect the sensing electrodes 106, 108 to the sensor interface 110 and to couple electrical signals from the sensor electrodes 106, 108 to the sensor interface 110.

The sensor interface 110 is integrated with, or attached to, the surface of the garment 1 at any suitable location on the garment 1.

The sensor assembly 104 is configured to derive biosignals such as electrocardiography, bioelectricity and bio-impedance signals as well as other measurements of biophysical parameters as may be appropriate. Such measurements are informative in monitoring health and fitness of a wearer, particularly during exercise. The data can then be communicated to the mobile device 102 for further processing analysis and display as required.

The sensing electrodes 106, 108 are arranged to contact the wearer's skin when the garment 1 is being worn.

In this exemplary embodiment, the sensing electrodes 106, 108 are provided on a first inner surface 2 of a main part of garment 1 so that they are located against the skin at a region of the wearer's body that enables biosignals to be sensed.

An outer surface 3 of the main part of the garment 1 faces away from the wearer's skin.

In the present embodiment, the sensing electrodes 106, 108 are ECG electrodes, but any other biosignal sensing electrode could be used in addition to, or instead of, the ECG electrodes. For example, EMG electrodes could be used. Other sensors such as position locations or motion sensors could also be used.

Figure 5:
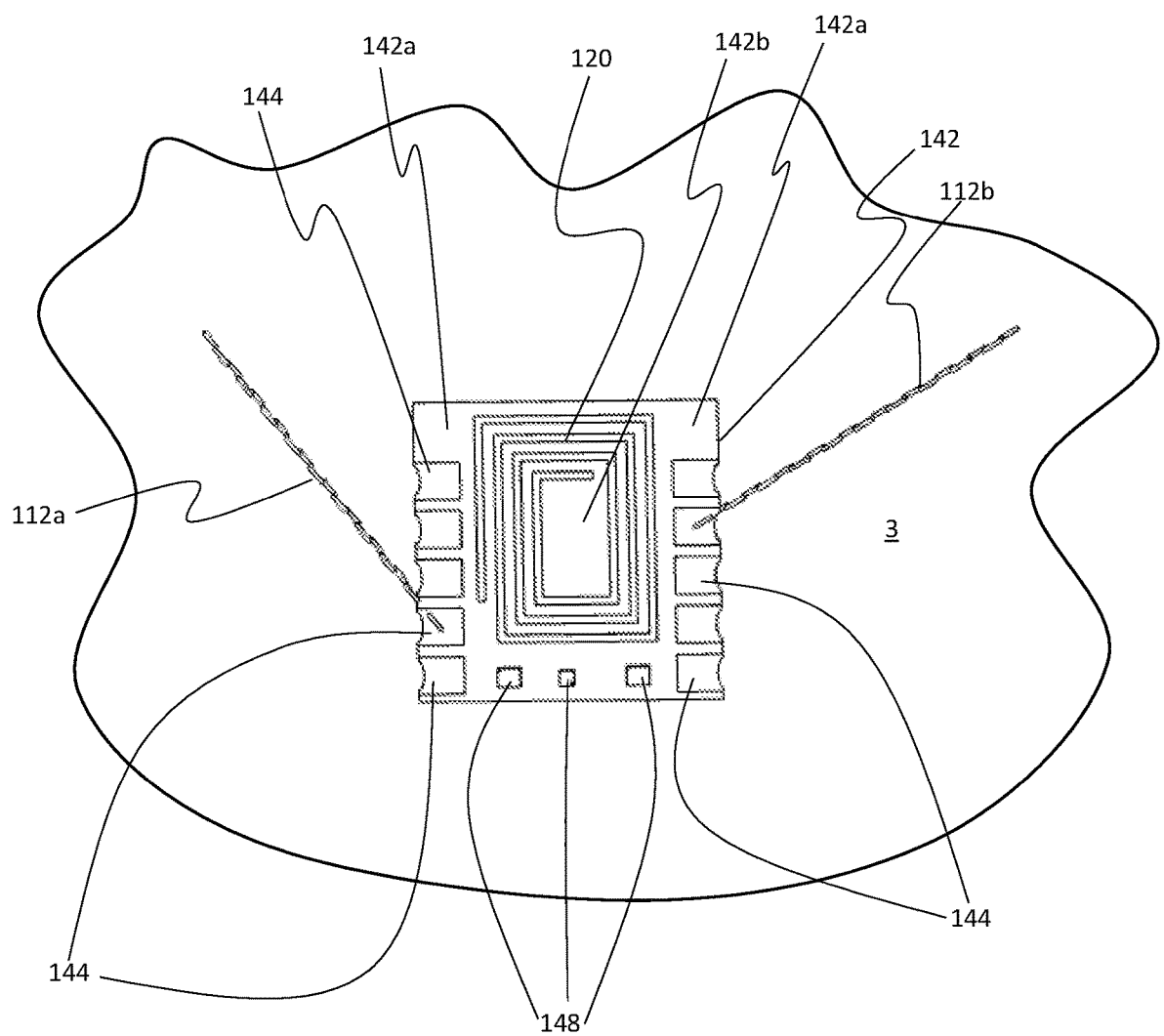
FIG. 5 is a schematic plan view of the printed circuit board of the sensor interface of FIG. 4.
Figure 6:
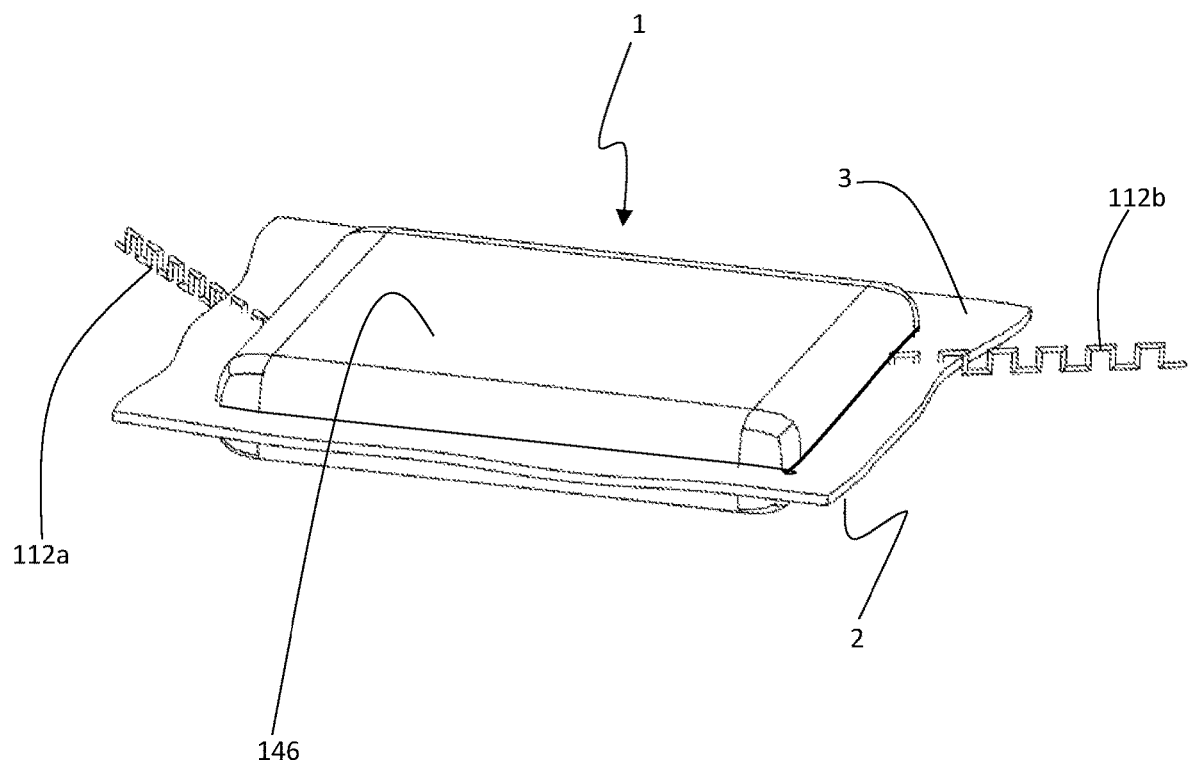
FIG. 6 is a perspective view of the sensor interface integrated with the fabric of a garment.

The conductors 112a, 112b are in the form of conductive threads woven into the garment 1, as illustrated schematically in FIGS. 5 and 6.

In the present disclosure, reference to a conductor being formed on the garment includes where the conductor is woven or otherwise formed within and integral to the garment.

In the embodiment described herein, the conductors 112a, 112b have a wavy configuration. The wavy configuration of the conductors 112a, 112b accommodates flexing, stretching and movement of the material without degrading them.

Other configurations of the conductors 112a, 112b can be used depending upon the application. For example, the conductors 112a, 112b can be linear.

Conductive threads are made from materials such as cotton or polyester incorporating metal or other electrically conductive fibres, or an electrically conducting coating. The metal can be any suitable electrically conductive metal such as silver, nickel, tin, copper or graphene. They can be sewn or woven in the same way as conventional yarns or threads.

The mobile device 102 contains the drive electronics which are configured to process incoming data from the sensor assembly 104 and transmit data to remote platforms as required.

The mobile device 102 can be detachably attachable to the garment 1 or otherwise held by the wearer of the garment 1 so that the wearer is able to bring the mobile device 1 into close proximity to the sensor assembly 104 to enable data to be transmitted between the mobile device 102 and the sensor assembly 104. In the exemplary embodiment, the mobile device 102 is detachably mounted adjacent to, and aligned with, the sensor interface 110 so that the mobile device 102 is in communication with the sensor interface 110.

The mobile device 102 includes at least an antenna in the form of an RF coil 124, a transceiver 126 and a power supply 152.

The mobile device 102 can be, for example, a cellular radio telephone, a WiFi device or any other suitable device configured for near field communication and wireless transmission. As mentioned above, the mobile device 102 includes the required drive electronics to provide the desired functionality.

In the embodiment described herein, the transceiver 126 is a mobile/cellular communicator operable to communicate the data wirelessly via one or more base stations in accordance with known protocols. The cellular communication network may be a fourth generation (4G) LTE, LTE Advanced (LTE-A), LTE Cat M1, LTE Cat M2, LTE Advanced (LTE-A) fifth generation (5G), sixth generation (6G), and/or any other present or future developed cellular wireless network.

Alternatively, or in addition, the transceiver 126 may provide wireless communication capabilities to communicate via one or more wireless communication protocols such as used for communication on: a wireless wide area network (WWAN), a wireless metro area network (WMAN), a wireless local area network (WLAN), a wireless personal area network (WPAN), a near field communication (NFC), a Bluetooth® module, Bluetooth® Low Energy, Bluetooth® Mesh, Bluetooth® 5, Thread, Zigbee®, IEEE 802.15.4, and Ant communication module, a Global Navigation Satellite System (GNSS), a cellular communication network, or any other electromagnetic RF communication protocol.

The mobile device 102 may further comprise a Universal Integrated Circuit Card (UICC) that enables the wearable article to access services provided by a mobile network operator (MNO) or virtual mobile network operator (VMNO). The UICC may include at least a read-only memory (ROM) configured to store an MNO/VMNO profile that the wearable article can utilize to register and interact with an MNO/VMNO. The UICC may be in the form of a Subscriber Identity Module (SIM) card. The mobile device 102 may have a receiving section arranged to receive the SIM card. In other examples, the UICC is embedded directly into a controller of the wearable article. That is, the UICC may be an electronic/embedded UICC (eUICC). A eUICC is beneficial as it removes the need to store a number of MNO/VMNO profiles, i.e. electronic Subscriber Identity Modules (eSIMs). Moreover, eSIMs can be remotely provisioned to garments. The mobile device 102 may comprise a secure element that represents an embedded Universal Integrated Circuit Card (eUICC).

A first communicator of the mobile device 102 may be provided for cellular communication and a separate communicator may be provided for short-range local communication over NFC, WLAN, WPAN Bluetooth®, WiFi, Bluetooth® module, Bluetooth® Low Energy, Bluetooth® Mesh, Bluetooth® 5, Thread, Zigbee®, IEEE 802.15.4, and Ant communication module or any other electromagnetic RF communication protocol.

The sensor interface 110 comprises a printed circuit board (PCB) 142 onto which sensing electronics, comprising circuitry and components 148 and a sensor interface antenna 120, is mounted.

In one embodiment, the PCB 142 is flexible. In another embodiment of the invention, the PCB 142 can include regions with differing flexibilities, where one region is more flexible than another. In the present embodiment, a region of increased flexibility 142a is provided at the perimeter region of the PCB, with a central region 142b being of reduced flexibility. The different levels of flexibility can be implemented, for example by applying a reinforcing layer in the regions of reduced flexibility or using different PCB thicknesses for the different regions so that the region of increased flexibility has a smaller thickness than the regions of reduced flexibility.

To achieve this, the PCB 142 may have a thickness in the region of reduced flexibility which is 0.05 mm or greater than the thickness of the PCB 142 in region of increased flexibility. This could be done, for example, by using a reinforcing layer with a thickness of 0.05 mm or more.

The sensing electronics is configured to process the signals from the sensing electrodes 106, 108 as described in further detail below. The sending electronics are provided on the region of reduced flexibility 142b.

Figure 4:
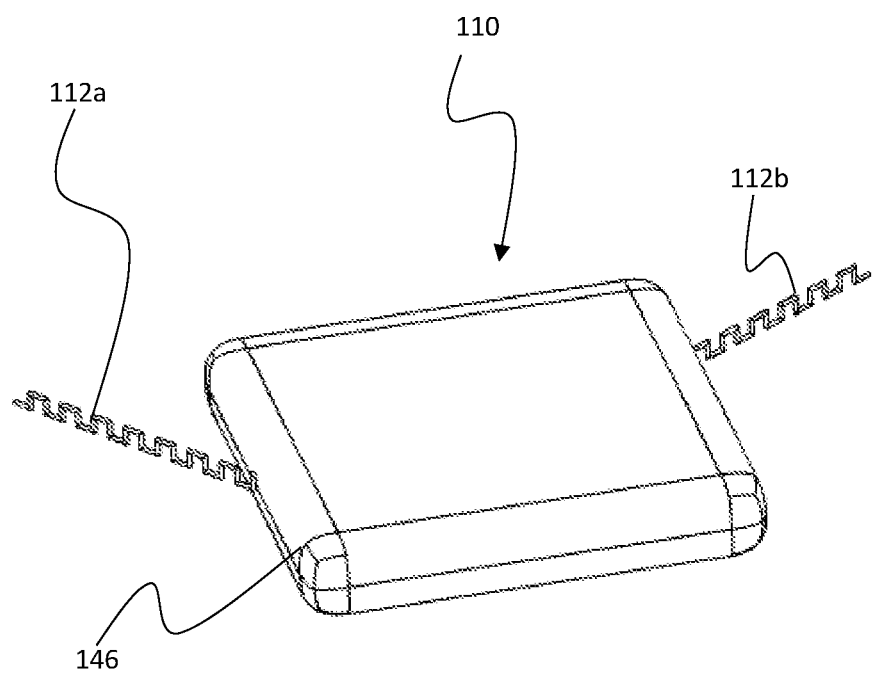
FIG. 4 is a perspective view of the sensor interface of the sensor assembly of FIG. 2.

The PCB 142 includes a plurality of terminals 144 at which the conductors 112a, 122b are terminated. In the exemplary embodiment, as illustrated in FIG. 4, the PCB 142 includes ten terminals 144 although only two are being used and to which the conductors 112a, 112b are connected. The plurality of terminals 144 are provided on a region of increased flexibility 142a.

The conductive threads that form the conductors 112a, 112b are formed into the garment 1 and terminate at the terminals 144. If additional sensing electrodes 106, 108 are being used, then these would be coupled to any of the unused terminals using conductive thread in the same way.

The conductors 112a, 112b are sewn, woven or embroidered into the garment 1 and connected to the respective terminal 144.

Alternatively, the conductors 112a, 112b are retained against a respective terminal 144 by a pressure fit.

The sensor interface 110 contains a microcontroller 116, an analogue front-end (AFE) 114 to interface with the sensing electrodes 106, 108 via the respective conductors 112a, 112b, a Near Field Communication (NFC) interface 118 and the sensor interface antenna in the form of an RF coil 120. These are all mounted on the PCB 142.

The microcontroller 116 communicates with the AFE 114 and with the NFC interface 118. The microcontroller 116 is powered by the NFC interface 118 and uses the NFC interface 118 to transmit data wirelessly from the sensor interface 110 to the mobile device 102.

The NFC interface 118 is operable to communicate with the mobile device 102 to exchange data therebetween.

In the present invention, therefore, the sensing electronics is arranged on the sensor interface 110, whilst the drive electronics is arranged on the mobile device 102 and acts as the primary data gatherer and a gateway to remote platforms and databases.

Data may be transferred between the NFC interface 118 and the mobile device 102 by means of inductive coupling between the two RF coils 120, 124 i.e. the antenna of the mobile device 102 and the antenna 124 of the sensor interface 110.

The sensor interface 110 is also powered by means of the inductive coupling and, as such, the sensor interface 110 does not have its own power supply.

The AFE 114 is selected for the application of the sensor interface. For example, the AFE 111 could be a MAX30001 produced by Maxim Integrated which is designed specifically for ECG applications.

For EMG applications, an ADS1298 AFE could be used, for example. The ADS1298 is manufactured by Texas Instruments Inc.

In this way, the sensors 106, 108 can sense and capture biosignals which can be transmitted as data to the sensor interface 110. The data can then be transferred to the mobile device 102 through near field communication in accordance with known near field communication protocols, so that the data can then be processed, stored and transmitted as needed, for example to a remote database, for display, or to a remote server for further processing.

The NFC interface 118 can be any suitable NFC device.

In the embodiment described herein the NFC interface 118 is the AS3956 NFC Dynamic Tag IC produced by AMS AG.

Figure 3:
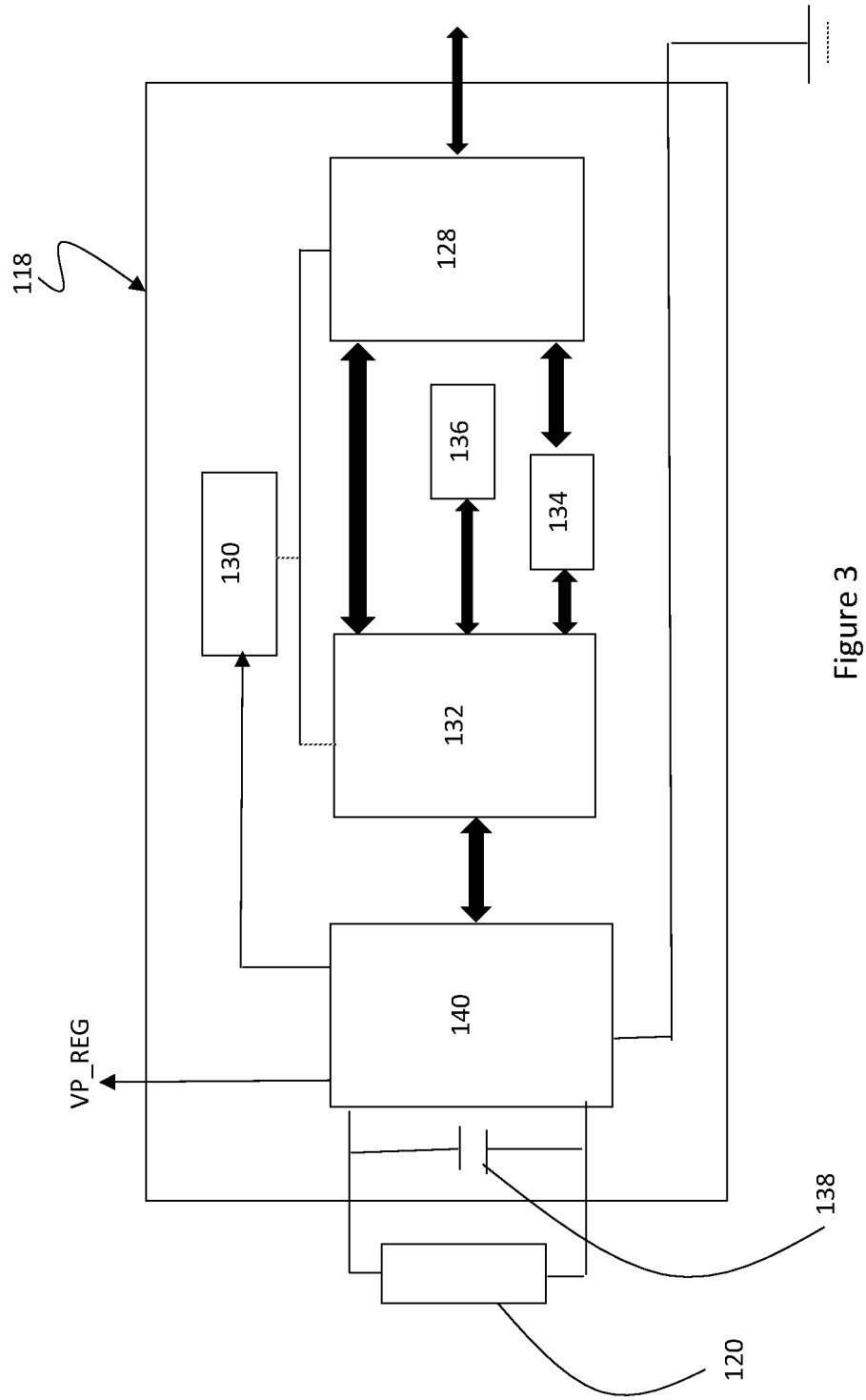
FIG. 3 a schematic block diagram illustrating the functional components of a near field communication interface of the sensor assembly of FIG. 2.

The NFC interface 118 is illustrated schematically in FIG. 3.

The NFC interface 118 includes an I²C/SPI interface 128, memory storage in the form an EEPROM 136, a buffer 134, a power manager 130, logic circuit 132 and an AFE 140. The AFE 140 is coupled to the RF coil 128 which forms, together with an integrated resonant capacitor 138, an LC circuit resonating with the external electromagnetic field frequency of 13.56 MHz.

At the presence of an RF field generated by the mobile device 102, the NFC interface 118 powers up the microcontroller 116 and handles an activation sequence.

The NFC interface 118 exchanges data with the mobile device 102 which can be stored in the EEPROM 136 or in an external memory (not shown). The microcontroller 116 can also exchange data with the NFC interface 118 via the I²C/SPI interface 128. The EEPROM 136 stores data including, for example, garment identification data. This data can be read from the EEPROM 136 whilst the microcontroller 116 is booting up with power provided through the proximity of the mobile device 102.

The AFE 140 has built-in rectifier and regulators. A regulator output VP_REG is available on a pin to supply external circuitry by harvesting energy from the RF field if required.

The power manager 130 controls the power supply of the logic circuit 132 and EEPROM 136 which is provided by the RF field induced in the antenna 120. The logic circuit 132 is responsible for data transfer. There is a 32-byte buffer 134 for block transmission between I²C/SPI interface 128 and the logic circuit 132. The EEPROM 136 is used to store a Unique Identifier (UID), configuration and control bits, and user data which can be accessed also via the I²C/SPI interface 128.

The EEPROM 136 can be easily updated through the NFC interface 118 at any stage.

The sensor assembly 104 is constructed by sewing, embroidering or riveting the PCB 142 onto the garment 1. The rivets could be mechanical rivets or they could be soldered or welded using conductive ink or glue, or spot welded.

The underside of the PCB 142 is adhesive lined, and the adhesive layer 154 is used to temporarily secure the PCB 142 to the surface of the garment 1 prior to connecting the PCB 142 to the conductors 112a, 112b.

The conductive thread forming the conductors 112a, 112b are sewn or embroidered or otherwise integrated into or formed on the garment 1 and stitched through the terminals 144 to provide an electrically conductive connection between the PCB 142 and the conductors 112a, 112b and then encased in an injection-moulded housing 146 to secure the PCB 142 to the garment 1. The housing 146 encloses the PCB 142 on the both the inner and outer surfaces 2, 3 of the garment 1. The use of a region of increased flexibility 142a where the terminals 144 are provided reduce the risk of the PCB 142 cracking when force is applied during the placing and securing of the PCB 142 onto the garment 1, or during use.

The PCB 142 is then permanently attached to the outer surface 3 of the garment 1 by means of the methods discussed above.

The housing 146 is made from a flexible material such as silicone rubber, with a shore of 85 or below and is moulded over the PCB 142 using injection moulding. The PCB 142 may be covered with an epoxy resin prior to the injection moulding of the housing 146.

The housing 146 provides protection from ingress of, for example, water. The use of a flexible material such as silicone rubber gives a soft feeling for the wearer of the garment 1 and an impression of invisibility.

The PCB 142, and the housing 146 are located on the garment 1 and placed at a location where the mobile device 102 can easily be located whilst enabling the two antenna 120, 124 to be aligned to enable communication between the sensor interface 110 and the mobile device 102. In the present invention, the garment 1 includes a pocket 150 into which the mobile device 102 can be placed. The pocket 150 is located and configured to ensure that the two antenna 120, 124 are aligned.

In use, when the mobile device 102 is powered up and brought into proximity to the sensor interface 110, and in response to the inductive coupling between the antenna 120, 124, the antenna 120 of the sensor interface 110 is energised which provides power to the NFC interface 118 which, in turn, provides power to the rest of the components 148 on the PCB 142.

Biosignals from the sensing electrodes 106, 108 are coupled to sensor interface 110 via the conductors 112a, 112b and the AFE 114.

The microcontroller 116 collates the biosignal data from the AFE 114 and transmits the data back, wirelessly, via the antenna 120 of the sensor interface 110 and the mobile device antenna 124 to the mobile device 102.

Configuration data (if required) and including garment identification data is stored in the EEPROM 136 and coupled to the mobile device 102.

The microcontroller 116 is operable to carry out minimal processing of the data such as data formatting. There is no complex processing which minimises power consumption within the sensor interface 110.

In alternative method of manufacturing of the garment 1, the conductors 112a, 112b are formed on, or integrated within, the garment 1 and arranged to terminate at a specific location on the garment 1. The specific location can be delineated using, for example, coloured yarn or thread or some other visual demarcation such a region of different texture or pattern.

The PCB 142 is then placed at the specific location using the location identifier to ensure that the PCB 142 is placed at the correct location on the garment 1.

The PCB 142 is held in place by means of the adhesive layer during the moulding the housing 146.

Figure 7:
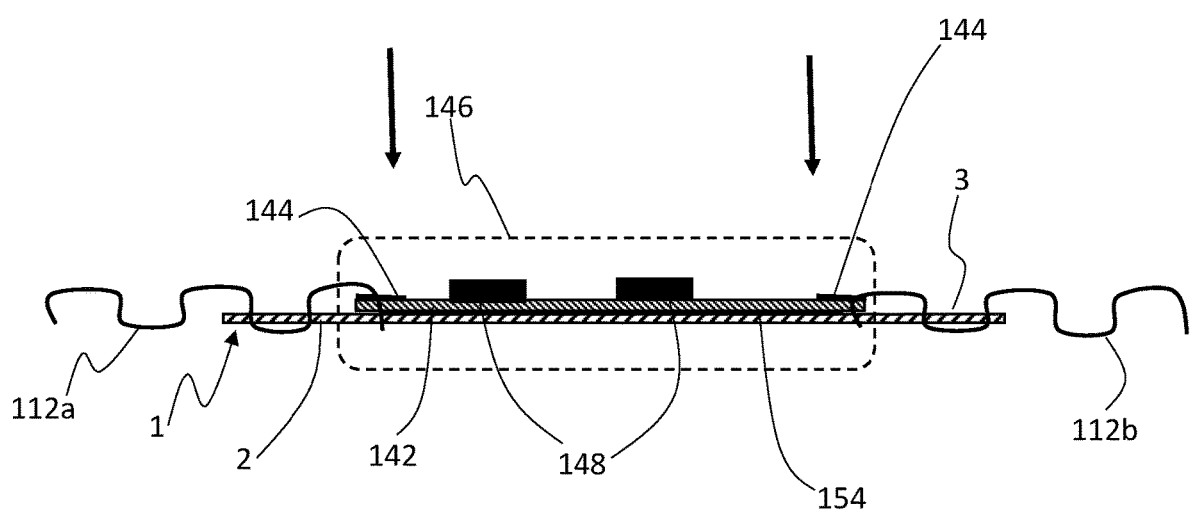
FIG. 7 is a schematic cross section of the sensor interface.

In addition, a number of pins (not shown) from, for example, a tooling jig can be used to apply a force—in the direction of the vertical arrows in FIG. 7—onto the PCB 142 to ensure that the PCB142, and in particular the respective terminals 144, are placed in electrical contact with the contacts 112a, 112b.

The housing 146 is then applied to the PCB 142 by injection moulding while the pins maintain PCB 142 in alignment with the contacts 112a, 112b during the moulding process. The pins can then be removed and the housing 146 retains the PCB 142, and in particular the contacts 144, in permanent contact with the conductors 112a, 112b.

In an alternative embodiment, the conductors 112a, 112b can be conductive transfers. Conductive transfers comprise thin, lightweight conductive elements which can be incorporated into flexible items such as fabrics and can therefore be used in wearable items such as items of clothing. Conductive transfers provide an electrically conductive pathway to an electronic device utilised as part of the clothing. Conductive transfers comprise a conductive layer, comprising mixture of silver ink (or other conductive ink), sandwiched between an inwardly-facing insulating layer and an outwardly-facing insulating layer.

Where the conductors 112a, 112b are conductive transfers, the inwardly facing layer is arranged such that, when the garment 1 is in use, the inwardly facing insulating layer faces the skin of the wearer.

Areas of the conductive layer can be exposed by forming the inwardly-facing insulating layer in sections such that the inwardly-facing layer has openings which expose areas of the conductive layer, and the sensing electrodes 106, 108 are formed where the conductive layer is exposed.

Conductive transfers are described in more detail in GB 2555592 B the disclosures of which are hereby incorporated by reference.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

Where conductive transfers are used, the terminating portions of the conductive transfers can be printed in a pattern that corresponds with the terminals 144 on the flexible PCB 142.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wearable article comprising a sensor assembly for sensing biosignals associated with a wearer of the wearable article, the sensor assembly comprising at least one biosignal sensor for sensing the biosignals, and a sensor interface coupled to the at least one biosignal sensor via a respective conductor, the sensor interface comprising sensing electronics including a sensor interface antenna, the sensing electronics being configured to collate biosignal data and to wirelessly communicate the biosignal data to the electronic device via the sensor interface antenna, and wherein the sensor interface comprises a flexible printed circuit board onto which the sensing electronics, including the sensor interface antenna, is mounted, the flexible printed circuit board including at least one terminal to which the sensing electronics are coupled, the respective conductor being connected to the at least one terminal, and wherein the respective conductor is formed from a conductive yarn stitched through the at least one terminal on the flexible printed circuit board and into the wearable article such that the flexible printed circuit board is permanently attached to an outer surface of the wearable article.

2. A wearable article according to claim 1, wherein the at least one terminal is provided on the region of increased flexibility.

3. A wearable article according to claim 1, wherein the flexible printed circuit board comprises a plurality of terminals and the sensor assembly comprises a plurality of biosignal sensors, each of the biosignal sensors being coupled to the sensor interface via the respective conductor and the respective conductor is connected one of the plurality of terminals.

4. A wearable article according to claim 1, wherein the sensor interface includes a housing arranged to encase the sensing electronics.

5. A wearable article according to claim 4, wherein the housing is made of a flexible material with a shore hardness of 90 or below.

6. A wearable article according to claim 1, wherein the at least one conductor is terminated in a delineated region of the wearable article and wherein the delineation is shown by a visible demarcation.

7. A system for measuring biosignals associated with a wearer of a wearable article, the system comprising the wearable article and an electronic device, the wearable article including a sensor assembly comprising at least one biosignal sensor for sensing associated biosignals, and a sensor interface coupled to the at least one biosignal sensor via a respective conductor, the electronic device comprising drive electronics, including an electronic device antenna and a power source, the sensor interface including a sensor interface antenna, the sensor interface antenna and the electronic device antenna being wirelessly coupled when the electronic device and the sensor interface are in close proximity, such that the sensing electronics is configured to collate biosignal data from the at least one biosignal sensor and to wirelessly communicate the biosignal data to the electronic device via the sensor interface antenna and the electronic device antenna, the sensor interface comprising a flexible printed circuit board onto which the sensing electronics is mounted, and the flexible printed circuit board includes at least one terminal to which the sensing electronics are coupled, wherein the respective conductor is connected to the at least one terminal, and wherein the respective conductor is formed from a conductive yarn stitched through the at least one terminal on the flexible printed circuit board and into the wearable article such that the flexible printed circuit board is permanently attached to an outer surface of the wearable article.

8. A system according to claim 7, wherein the flexible printed circuit board has a region of increased flexibility, and the at least one terminal to which the at least one sensing electrode and the sensing electronics are coupled is provided on the region of increased flexibility.

9. A system according to claim 7, wherein the flexible printed circuit board comprises a plurality of terminals and the sensor assembly comprises a plurality of biosignal sensors, each of the biosignal sensors being coupled to the sensor interface via the respective conductor and wherein the respective conductor is connected to a terminal of the plurality of terminals.

10. A system according to claim 7, wherein the sensor interface includes a housing made of a flexible material arranged to encase the sensing electronics.

11. A system according to claim 10, wherein the housing is made of a flexible material with a shore hardness of 90 or below.

12. A system according to claim 7, wherein the sensing electronics includes a controller, and an interface arranged to couple the biosignal data from the at least one biosignal sensor to the sensing electronics and a wireless interface configured to couple the biosignal sensor data to the sensor interface antenna for wireless communication to the electronic device antenna.

13. A system according to claim 7, wherein the sensing electronics is configured to receive power from the electronic device via the electronic device antenna and the sensor interface antenna.

14. A system according to claim 13, wherein the interface is a short-range communication module.

15. A system according to claim 7, wherein the at least one conductor is terminated in a delineated region of the wearable article and wherein the delineation is shown by a visible demarcation.

16. A system according to claim 7, wherein the sensor interface antenna is inductively coupled to the electronic device antenna.

17. A method of manufacturing a wearable article including a sensor assembly for sensing biosignals associated with a wearer of the wearable article, the method including the steps of:
forming at least one biosignal sensor on the wearable article;
forming a flexible printed circuit board having a region of increased flexibility;
mounting sensor electronics on the flexible printed circuit board, the sensing electronics including an antenna and at least one terminal;
forming at least one conductor from a conductive yarn on the wearable article so as to electrically couple the at least one biosignal sensor and the at least one terminal;
stitching through the at least one terminal on the flexible printed circuit board and into the wearable article such that the flexible printed circuit board is permanently attached to an outer surface of the wearable article; and
forming a housing around the flexible printed circuit board to encase the sensor electronics.

18. A method according to claim 17, wherein the at least one terminal is formed on the region of increased flexibility.

19. A method according to claim 17, wherein the flexible printed circuit board is formed to be thinner at the region of increased flexibility.

20. A method according to claim 17, wherein the flexible printed circuit board includes a region of reduced flexibility, and the region of reduced flexibility may be formed by adding a reinforcing layer.

21. A method according to claim 17, wherein the method includes the step of covering the flexible printed circuit board with an epoxy resin prior to forming the housing around the flexible printed circuit board.

22. A method according to claim 17, wherein the at least one conductor is terminated in a region of the wearable article, and wherein the region is delineated, the delineation being shown by a visible demarcation.

23. A method according to claim 17, wherein the housing is formed by injection moulding.

* * * * *